United States Patent
Varlet et al.

(10) Patent No.: US 11,986,335 B2
(45) Date of Patent: May 21, 2024

(54) DENTAL IMAGING APPARATUS WITH AN INTEGRATED MOVABLE SEAT ARRANGEMENT

(71) Applicant: Trophy, Croissy-Beaubourg (FR)

(72) Inventors: Stephane Varlet, Croissy-Beaubourg (FR); Yann Lecuyer, Croissy-Beaubourg (FR); Olivier Nesme, Croissy-Beaubourg (FR)

(*) Notice: Subject to any disclaimer, the term of this patent is extended or adjusted under 35 U.S.C. 154(b) by 10 days.

(21) Appl. No.: 16/472,469

(22) PCT Filed: Dec. 22, 2016

(86) PCT No.: PCT/IB2016/002001
§ 371 (c)(1),
(2) Date: Jun. 21, 2019

(87) PCT Pub. No.: WO2018/115922
PCT Pub. Date: Jun. 28, 2018

(65) Prior Publication Data
US 2021/0128088 A1    May 6, 2021

(51) Int. Cl.
*A61B 6/00* (2006.01)
*A61B 6/04* (2006.01)
*A61B 6/51* (2024.01)

(52) U.S. Cl.
CPC .............. *A61B 6/51* (2024.01); *A61B 6/0478* (2013.01); *A61B 6/4452* (2013.01)

(58) Field of Classification Search
CPC .............................. A61B 6/14; A61B 6/0478
See application file for complete search history.

(56) References Cited

U.S. PATENT DOCUMENTS 5,692,027 A * 11/1997 Yoshimura ............... A61B 6/14
378/116

* cited by examiner

*Primary Examiner* — Dani Fox

(57) ABSTRACT

The invention concerns an extra-oral dental imaging apparatus for obtaining a radiographic image of a patient, the apparatus comprising:—a support frame,—a gantry that supports an x-ray source and at least one x-ray sensor in correspondence with the x-ray source, the gantry being movable relative to the support frame, wherein the apparatus further comprises a seat arrangement that is connected to the support frame and that is movable between at least two distinct positions: a working position in which the seat arrangement is located in a working area under the gantry, at least one rest position in which the seat arrangement is located away from the working area so as to leave clear the working area under the gantry.

20 Claims, 8 Drawing Sheets

DENTAL IMAGING APPARATUS WITH AN INTEGRATED MOVABLE SEAT ARRANGEMENT

FIELD OF THE INVENTION

The invention relates generally to the field of extra-oral dental x-ray imaging.

BACKGROUND OF THE INVENTION

A conventional extra-oral dental x-ray imaging apparatus generally comprises:
- a support frame
- a movable gantry that supports an x-ray source and an x-ray sensor in correspondence with the x-ray source and that is movable relative to the support frame.

When the apparatus is being operated for obtaining a radiographic dental image of a patient's head, the patient is generally standing up under the gantry and positioned between the x-ray source and the x-ray sensor.

The x-ray source is energized so as to generate an x-ray beam which radiates the teeth of the patient before impinging the x-ray sensor. The gantry is driven into motion and follows a given path according to the imaging process.

For certain persons, such as elderly people and young patients, standing proves to be difficult.

Also, for certain types of imaging process the head of the patient has to stay motionless while the imaging process is being operated.

This is difficult for most people and even more problematic for the above-cited persons.

It would then be desirable to provide an apparatus and a method that take into account the above.

SUMMARY

It is an object of the present disclosure to advance the art of dental extra-oral imaging. Another object of this application is to address, in whole or in part, at least the foregoing and other deficiencies in the related art. It is another object of this application to provide, in whole or in part, at least the advantages described herein.

According to an aspect, an extra-oral dental imaging apparatus for obtaining a radiographic image of a patient, comprises:
- a support frame,
- a gantry that supports an x-ray source and at least one x-ray sensor in correspondence with the x-ray source, the gantry being movable relative to the support frame,
- wherein the apparatus further comprises a seat arrangement that is connected to the support frame and that is movable between at least two distinct positions:
  - a working position in which the seat arrangement is located in a working area under the gantry,
  - at least one rest position in which the seat arrangement is located away from the working area so as to leave clear the working area under the gantry.

Certain exemplary method and/or apparatus embodiments can integrate a movable seat and makes it possible for patients to stay sitted on the seat in the working position during the whole imaging process. When the imaging process has come to an end or when the patient is able to do without the seat, the seat is moved into the at least one rest position. This is a simple and reliable arrangement of the apparatus.

According to possible features:
- the seat arrangement comprises a seat assembly and a connecting arm;
- the seat assembly comprises a seat part and a leg assembly for ground support;
- the seat arrangement is configured to pivot relative to the support frame;
- the seat arrangement is configured to pivot relative to the support frame through a pivoting assembly;
- the support frame comprises an indexed face which includes at least two indexed positions corresponding to said at least two distinct positions of the seat arrangement respectively, the seat arrangement being configured to pivot relative to the indexed face through the pivoting assembly to move from one indexed position to another;
- the indexed face includes three indexed positions corresponding to three distinct positions of the seat arrangement respectively, namely the working position and two rest positions;
- the seat arrangement is urged against the indexed face through at least one elastic member;
- the seat arrangement comprises a connecting member that connects the connecting arm to the support frame, the connecting member being configured to pivot at one end relative to the indexed face through the pivoting assembly to move from one indexed position to another;
- the connecting member is connected at its opposite end to a first end of the connecting arm, the second opposite end of the connecting arm being connected to the seat assembly;
- the first end of the connecting arm is movably mounted relative to the connecting member in a vertical plane that includes the pivot axis of the pivoting assembly;
- the first end of the connecting arm is urged upwardly through at least one elastic member so that the connecting arm is urged in an upper rest position in the absence of any patient on the seat assembly;
- the first end of the connecting arm is pivotally mounted relative to the connecting member about a pivot axis that is perpendicular to the vertical plane;
- the seat arrangement is configured to both pivot and translate relative to the support frame (C4);
- the connecting arm is an hinged arm.

According to another aspect, a method for using an extra-oral dental imaging apparatus for obtaining a radiographic image of a patient, comprises:
- a support frame,
- a gantry that supports an x-ray source and at least one x-ray sensor in correspondence with the x-ray source, the gantry being movable relative to the support frame,
- a seat arrangement that is connected to the support frame,
- wherein the method comprises moving the seat arrangement between at least two distinct positions:
  - a working position in which the seat arrangement is located in a working area under the gantry,
  - a rest position in which the seat arrangement is located away from the working area so as to leave clear the working area under the gantry.

According to possible features:
- moving the seat arrangement comprises pivoting the seat arrangement relative to the support frame about a pivot axis;
- moving the seat arrangement further comprises translating the seat arrangement relative to the support frame;

the seat arrangement comprises a seat assembly and a hinged connecting arm and moving the seat arrangement comprises folding or unfolding the hinged connecting arm.

These objects are given only by way of illustrative example, and such objects may be exemplary of one or more embodiments of the invention. Other desirable objectives and advantages inherently achieved by the disclosed methods may occur or become apparent to those skilled in the art. The invention is defined by the appended claims.

BRIEF DESCRIPTION OF THE DRAWINGS

Other features and advantages will appear in the course of the remainder description, made by way of non-limiting examples, with reference to the following drawings.

DETAILED DESCRIPTION OF EXEMPLARY EMBODIMENTS

Figure 1:
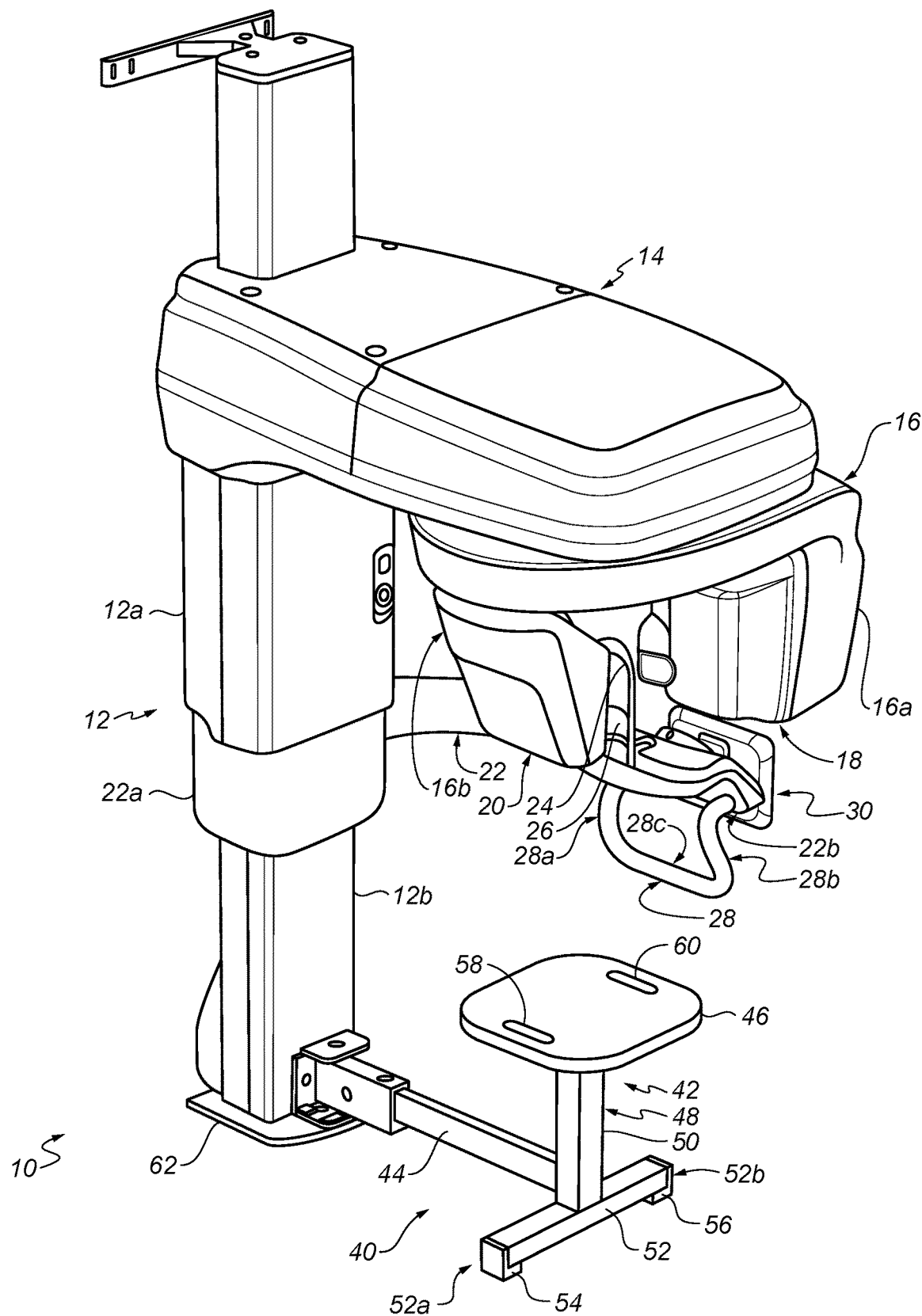
FIG. 1 depicts an overall schematic perspective view of an extra-oral imaging apparatus according to an embodiment of the invention.

FIG. 1 illustrates an embodiment of an extra-oral imaging apparatus 10. Apparatus 10 comprises a support structure that includes a support frame 12 which may be a support column. The column 12 may be adjustable in two or three dimensions. For example, the column 12 can be telescopic and may include an upper part 12a that is slidably mounted over a fixed lower part 12b.

The support structure also includes a horizontal mount 14 that may be supported or held by the vertical column 12. Horizontal mount 14 extends away from vertical column 12 and may be substantially perpendicular thereto. Horizontal mount 14 can move relative to the vertical column 12. More particularly, horizontal mount 14 is fixedly mounted on the vertical upper part 12a and is therefore movable therewith. For example, an actuator, e.g. of the electric type, located behind the vertical column (not represented in the drawing) can be commanded to drive the horizontal mount 14 into a vertical movement in a controlled manner. Horizontal mount 14 can support a gantry 16. Gantry 16 is movable relative to the support structure, and more particularly to horizontal mount 14. Gantry 16 may more particularly be rotatable relative to horizontal mount 14. Gantry 16 may be rotatable about a vertical axis of rotation, which may be still during the operation of the imaging process or may follow one among several predetermined trajectories, in accordance with the selected imaging process. A driving known mechanism (not represented) for driving the gantry 16 into a given movement is integrated inside horizontal mount 14. By way of example, such driving mechanism includes motors for imparting a first movement in a X, Y plane, e.g. two step by step motors, and a motor for imparting a rotational movement about the vertical axis Z, e.g. a brushless motor.

Gantry 16 supports both an x-ray source 18 and at least one x-ray sensor 20 that is arranged in correspondence with the x-ray source. X-ray source 18 and the at least one x-ray sensor 20 may be arranged facing each other. Gantry 16 may include two opposite downwardly extending arms: a first arm 16a supports x-ray source 18 that is attached thereto and a second opposite arm 16b supports the at least one x-ray sensor 20 that is attached thereto.

When activated x-ray source 18 emits an x-ray beam which radiates all or part of an imaging area, e.g., a working area for placement of the patient's head, before impinging the at least one x-ray sensor 20.

In the present embodiment, the at least one x-ray sensor 20 may include a panoramic sensor, e.g. a slit-shaped sensor, a volumetric or computerized sensor (e.g. rectangular, square-shaped) or a cephalometric sensor or several sensors.

Depending on the sensor or sensors present in the apparatus, one or several operating modes or imaging processes (1, 2 or 3) may be used among the panoramic, volumetric or computerized tomography, and cephalometric modes. The support structure may also include a patient positioning arm 22 that is connected to the support frame, and more particularly to the vertical column 12. The patient positioning arm 22 is movable relative to the support frame. More particularly, arm 22 can slide along the vertical column 12 so as to move up or down upon command. The patient positioning arm 22 extends from an arm support 22a that is slidably mounted relative to the fixed lower part vertical column 12b. The patient positioning arm 22 extends along the apparatus in a direction that is substantially in correspondence with the direction of extension of horizontal mount 14. Patient positioning arm 22 is arranged sideways relative to the apparatus in a substantial parallel relationship with horizontal mount 14. For example, an actuator, e.g. of the electric type, located behind the vertical column (not represented in the drawing) can be commanded to drive the arm support 22a into a vertical movement in a controlled manner.

Patient positioning arm 22 serves to position the patient in the apparatus at a given location. In one embodiment, the patient positioning arm 22 can position the patient in the imaging area according to selection of an operating modes of the apparatus 10.

Patient positioning arm 22 may include one or more patient positioning and/or holding systems generally located at a free end 22b of the arm or proximate thereto.

One or more patient positioning and/or holding systems allow to position the anatomical structures of the patient's head according to different orientations and to immobilize the patient's head during the examination so as to reduce any possible movement.

There exists one or several systems for each type of examination to be carried out. The arm 22 is configured to accommodate these systems.

As illustrated in FIG. 1, one of these systems, noted 24, includes two temporal holding members that extend upwardly from the arm 22 to which they are removably attached. Only one temporal holding member is represented, the other one being hidden by the arm 16b.

Another illustrated system is a chin support 26 that extends upwardly from the arm 22 to which it is removably attached. The chin support 26 can be located between the two temporal holding members.

Other possible attachable, movable or integrated systems may be envisaged: a nasal support, a bite support etc.

A handle assembly 28 may be positioned at the free end 22b of the arm, underneath the arm and in a parallel relationship with the arm. This handle assembly 28 includes two vertical separate handle portions 28a, 28b which can be grasped by the patient when undergoing an imaging process so as to remain motionless.

Overall this handle assembly 28 has a U-shape which can include a horizontal base portion 28c and two vertical upwardly-extending branches 28a, 28b that are fixed to the arm 22. Each branch plays the role of a vertical handle portion.

Patient positioning arm 22 also supports a monitor or display assembly 30 which makes it possible for a user of the apparatus to view and drive certain functions of the apparatus.

The apparatus 10 further comprises a seat arrangement 40 that is connected to the support frame 12. The seat arrangement 40 is movable between at least two distinct positions:
- a working position in which the seat arrangement 40 is located in a working area with a prescribed spatial relationship to the the gantry 16 and the horizontal mount 14 (FIG. 1, e.g., below or under),
- at least one rest position in which the seat arrangement 40 is located away from the working area so as to leave clear the working area under the gantry 16.

Figure 2:
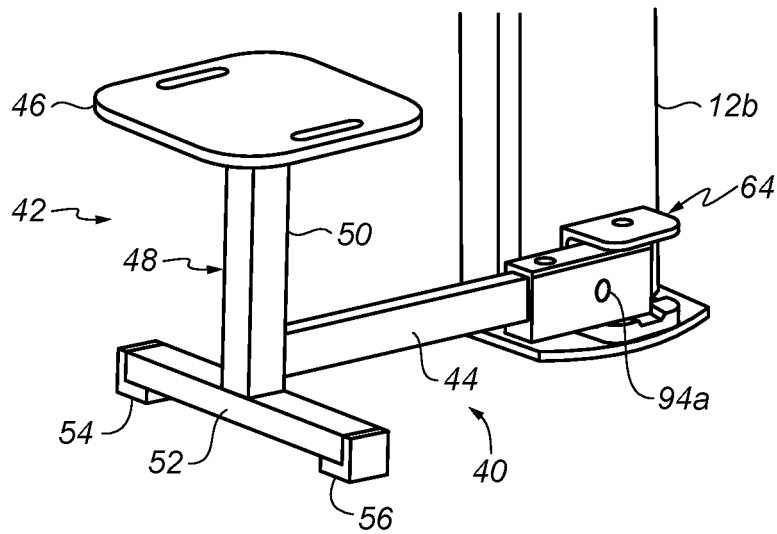
FIGS. 2 and 3 illustrate two rest positions of the seat arrangement of FIG. 1.
Figure 3:
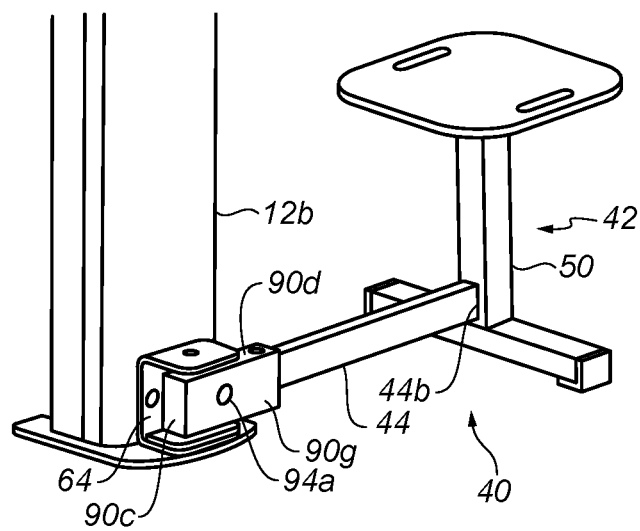

FIGS. 2 and 3 illustrate two example different possible rest positions for the seat arrangement 40 (the remainder of the apparatus has not been represented by virtue of simplicity): the seat arrangement occupies two diametrically opposed rest positions that are preferably disposed at 180° one from another. However, other embodiments can envision an angle between rest positions greater than 180° or less than 180° (e.g., up to 270° or less than 90°). The working position in FIG. 1 can be a median position relative to the two extreme symmetric rest positions. Alternatively, the angle between the working position and a desired rest position can be up to 180°. Also, the working position in FIG. 1 can be an offset position closer to one or the two extreme symmetric rest positions. In FIG. 1 the seat arrangement 40 is located below the gantry 16 and the horizontal mount 14 and in parallel relationship therewith. In each of the two rest positions the seat arrangement 40 is no longer below gantry 16 and horizontal mount 14 and, for example, is at an angle of 90° to horizontal mount 14.

Certain exemplary method and/or apparatus embodiments can reciprocally move the seat arrangement 40 repeatedly between various different positions described above. For example, in one embodiment, seat arrangement 40 is configured to pivot relative to the support frame 12 through a pivoting assembly to enable rotation of the seat arrangement between the different positions described above.

As depicted in FIGS. 1 to 3, the seat arrangement 40 may comprise a seat assembly 42 and a connecting arm 44. The seat assembly 42 may comprise a seat part 46 and a leg assembly 48 for ground support. Leg assembly 48 may comprise a vertical central supporting member 50 and a horizontal transverse member 52 which carries supporting member 50 and may be a bar. Transverse member 50 is provided at its two opposite ends 52a, 52b with pads 54 and 56 which are located under the transverse member and on the side opposite ends thereof. Pads 54 and 56 allow to keep the transverse member raised above the ground.

The seat assembly 42 may comprise slots 58 and 60, e.g. elongated slots, that are formed through its thickness and located proximate its outer periphery. Slots 58 and 60 play the role of handling portions for manually handling the seat assembly 40 and moving it from the median working position of FIG. 1 towards one of the two extreme rest positions of FIGS. 2 and 3 and the reverse. Slots 58, 60 may be arranged on two opposite sides of the seat assembly for handling the seat assembly more easily and conveniently.

More particularly, column 12 is supported at its lower end by a baseplate or supporting plate 62 and seat arrangement 40 is connected to baseplate 62 through the above-mentioned pivoting assembly. The fixed lower part 12b is coupled to baseplate 62.

Figure 4:
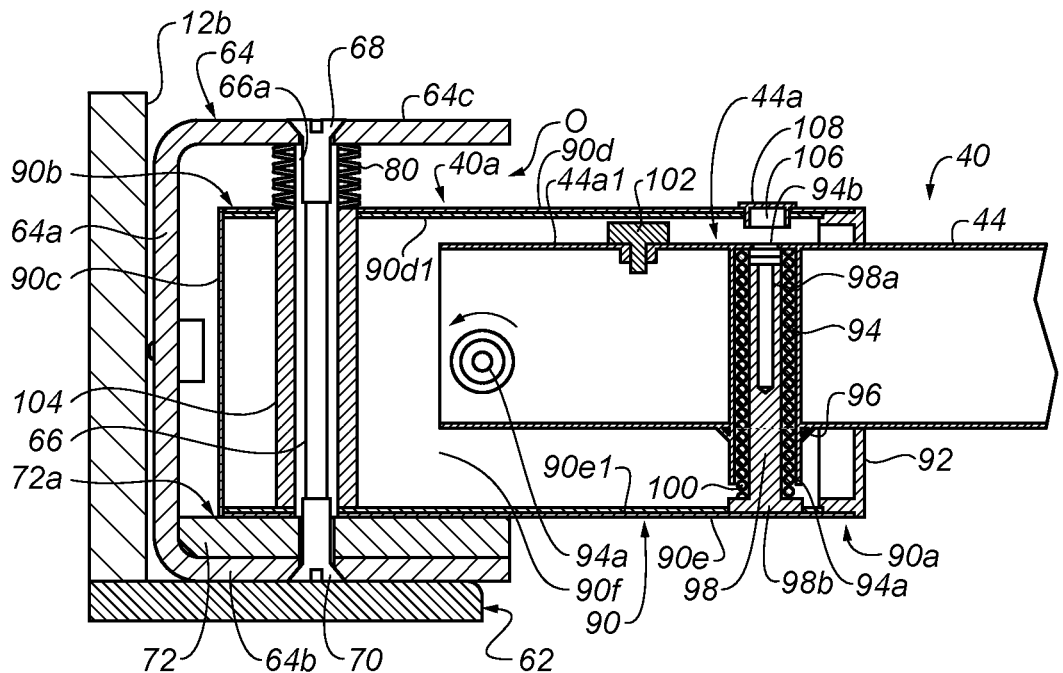
FIG. 4 is an enlarged partial longitudinal cross-section of the connection zone between the connecting arm of the seat arrangement of FIG. 1 and the support frame.

The connection of the seat arrangement 40 to the support frame 12 is further detailed on FIG. 4 which is an enlarged view of the connecting zone in a longitudinal cross-section of the seat arrangement.

A mounting bracket 64 is fixed to baseplate 62 through conventional permanent, fixed or re-attachable fastening members, e.g. screws, not represented here for the sake of clarity.

Mounting bracket 64 has for example a C shape whose opening O is oriented opposite the column 12. Mounting bracket 64 comprises three portions: a middle portion 64a that is vertically oriented with its back to the column 12, a lower portion 64b that is horizontally oriented and rests against baseplate 62 to which it is fixed and an upper horizontal portion 64c facing the lower portion 64b. Both lower and upper portions 64b and 64c are adjacent the middle portion and conjointly define therewith the opening O.

The above pivoting assembly is mounted in connection with mounting bracket 64 at one free end 40a of the seat arrangement 40 through a pivoting hollow axis 66 that is vertically disposed between the upper and lower portions 64c and 64b. Hollow axis 66 is fastened to upper and lower portions 64c and 64b through respective fastening members 68 and 70, e.g. screws. Fastening members 68 and 70 are respectively engaged into two threaded hollow ends of the axis 66 through the outside face of each of the upper and lower portions 64c and 64b.

More particularly, an indexed support or pad 72 is inserted between the seat arrangement end 40a and the upper face of the lower portion 64b and fixed to the latter. Indexed pad 72 comprises an indexed upper face 72a that is in contact with the seat arrangement end 40a in FIG. 4 and is configured to include three distinct indexed positions that are represented from above in FIG. 5. Indexed upper face 72a is configured to include four raised portions each located at one of the four corners of the face: two separate raised portions 74b and 74c defining therebetween a first space S1 and two other separate raised portions 74d and 74e of greater dimensions defining therebetween a second reduced space S2. Raised portion 74b and larger raised portion 74d define therebetween a space S3 preferably of the same width as the second reduced space S2. Raised portion 74c and larger raised portion 74e define therebetween a space S4 preferably of the same width as the second reduced space S2.

Spaces S2, S3 and S4 between the corresponding raised portions allow each to accommodate the seat arrangement end 40a in one of the three indexed positions each being in register with one of the working position and the two rest positions. In the working position seat arrangement end 40a occupies space S2 (more specifically, a portion of the lower face of end 40a lies in space S2 against face 72a) and extends to a location disposed between smaller raised portions 74b and 74c.

Smaller raised portions 74b and 74c enable positioning of through holes 76, 78 therebetween while leaving sufficient room for accommodating seat arrangement end 40a in the working indexed position between holes 76, 78. These holes allow to accommodate fastening members (not represented for the sake of simplicity) for fastening indexed pad 72 to lower portion 64b.

Figure 5:
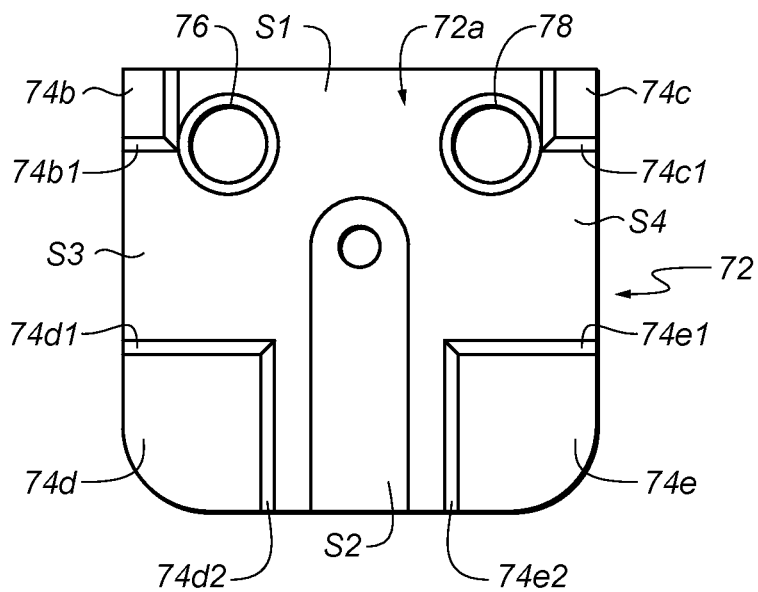
FIG. 5 is an enlarged top view of an indexed plate.
Figure 6:
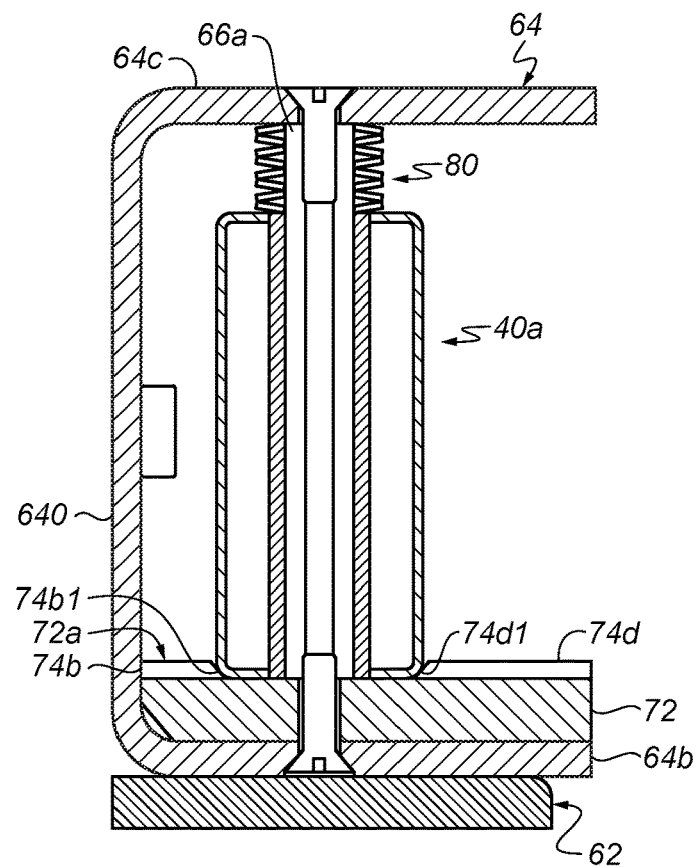
FIG. 6 is an enlarged partial transverse cross-section of the connection zone of FIG. 4.

FIG. 6 is an enlarged view in a transverse cross-section of the seat arrangement end 40a that has been moved from the working indexed position to the rest indexed position defined by space S3 of FIG. 5.

FIG. 6 illustrates beveled edges 74b1 and 74d1 of the respective raised portions 74b and 74d and end 40a is positioned between these beveled edges.

A similar arrangement is provided for the other raised portions with beveled edges 74d2, 74e2, 74e1 and 74c1 located on either side of the corresponding space S2 and space S4. Each pair of beveled edges define together with the corresponding central space a groove in which end 40a can be positioned.

Overall beveled edges make it easier the motion (e.g., rotary) of the end 40a from one indexed position towards another adjacent one. Beveled edges act as ramps that guide and help end 40a to leave the groove. Other known conventional edges, sides or transitions can be used to make easier the motion of the end 40a from one indexed position towards another adjacent one.

As illustrated in FIGS. 4 and 6, the seat arrangement 40 is urged against indexed pad 72 through at least one elastic member 80. Elastic member 80 is disposed around a protruding end portion 66a of axis 66 that extends between end 40a and upper portion 64c. Elastic member 80 is maintained in this position in a compressed state, which biases the end 40a downwardly against the corresponding indexed position (working position in FIG. 4 and a rest position in FIG. 6). Thus, the seat arrangement is forcibly maintained in one of the three indexed positions thanks to elastic member 80. By way of non-limiting example, elastic member 80 may be a spring or an arrangement composed of several springs.

The above seat arrangement and its moving mechanism provides a convenient and reliable arrangement to the apparatus. Thanks to this new arrangement the imaging process will be operated in reproducible or optimized conditions for the patients: the elderly and young patients will sit under the gantry during the process. This is also useful for tall persons who may encounter difficulties when standing under the gantry.

Once the imaging process is terminated, the seat arrangement can be easily and quickly moved into a rest position so as to leave the working position unobstructed.

All that has been described above regarding the pivoting assembly of the seat arrangement 40 applies as well to a seat arrangement deprived of any specific configuration at its free end. Such a seat arrangement has only a connecting arm the end of which is arranged to be pivotally mounted about axis 66.

A more detailed exemplary possible embodiment of the seat arrangement 40 will now be described. This embodiment illustrates a specific configuration of the seat arrangement end 40a that is illustrated on FIGS. 1 to 4.

In this respect, the seat arrangement 40 comprises a connecting member 90 that connects the connecting arm 44 to the support frame. In this embodiment the connecting arm 44 is not directly connected to the support frame and connecting member 90 longitudinally extends connecting arm 44. In this embodiment, the connecting member 90 has, e.g. an elongated hollow shape, and two opposite ends:

a first end 90a that is configured to be connected to a first end 44a of arm 44;
  a second end 90b that is configured to be pivotally mounted relative to the indexed face 72a through the above-described pivoting assembly in order to move the connecting member 90 and, therefore, the whole seat arrangement 40, from one indexed position to another.

The second opposite end 44b of the connecting arm 44 is connected to the supporting member 50 of seat assembly 42 (FIG. 3).

First end 90a is configured to enable insertion of the first end 44a of arm 44 inside the longitudinal hollow connecting member 90 and is temporary closed by a removably inserted plug 92. Plug 92 is perforated so as to be traversed by first end 44a.

In the present embodiment, the connecting member 90 is in the form of a hollow casing which comprises five walls 90c-g illustrated on FIGS. 3 and 4 taken conjointly: an end vertical wall 90c that closes end 90b, two opposite upper and lower walls 90d and 90e and two opposite side walls 90f, 90g. Walls 90d-g conjointly define open end 90a that is closed by plug 92 and traversing arm 44.

The first end 44a is connected to connecting member 90 through a horizontal pivot axis 94a about which first end 44a is pivotally mounted. Pivot axis 94a is inserted through perforations provided in walls 90f and 90g and end 44a and in register therewith.

The first end 44a, or a terminal portion of the arm proximate the first end 44a, is also elastically mounted on an inner face 90e1 of lower wall 90e. First end 44a is configured to include a cavity 94 that is arranged transversally relative to the longitudinal axis of arm 44 and that is open at its two opposite lower and upper ends 94a, 94b. The cavity 94 is defined by a transverse wall 96 that extends over the whole height of the arm 44 and protrudes downwardly from the lower face of end 44a. A vertically-oriented rod 98 is rests against the inner lower face 90e1 and may be couple thereto. Rod 98 serves as a support axis for at least one elastic member 100 arranged around the rod. The at least one elastic member 100 and rod 98 are both housed inside cavity 94 and the at least one elastic member 100 is in a compressed state, thus urging first end 44a upwardly. The at least one elastic member 100 may, e.g. comprise a spring.

An elastomer pad 102 is disposed on the outer face of upper portion 44a1 of first end 44a so as to serve as a mechanical stop against the inner face 90d1 of upper face 90d when connecting arm 44 is urged upwardly under specific conditions.

Second end 90b of connecting member 90 includes a vertically-extending sheath 104 that is arranged between two upper and lower holes provided in the respective upper and lower walls 90d and 90e. Sheath 104 is fixed to walls 90d and 90e and surrounds axis 66.

To be noted that hole 94b is used for mounting arm end 44a inside connecting member 90. The mounting operation starts with insertion of elastic member 100 and rod 98 surrounded by elastic member inside cavity 94. A screw (not represented) is then inserted through hole 94b into the innerly threaded end 98a of rod 98. This temporary arrangement ties elastic member 100 and rod 98 together with arm 44, which makes it possible to longitudinally introduce arm 44 partially inside hollow connecting member 90. The arm is introduced to a longitudinal position where the perforations in walls 90f and 90g are in register with perforations in end 44a and a hole 106 provided in the upper wall 90d is in register with hole 94b. In this position the head 98b of rod 98 rests against inner face 90e1. Axis 94a is horizontally inserted through the corresponding perforations and fixedly mounted thereto so as to link arm 44 to connecting member 90 through a pivotally mounting. Also, the screw fixed into the threaded end 98a or rod 98 is unscrewed from above through hole 106. Elastic member 100 can then partially extend inside cavity 94 and urge end 44a upwardly. A plug 108 is next introduced into hole 106 to seal it.

The position of the seat arrangement 40 illustrated in FIG. 4 corresponds to the situation where a patient is on the seat part 46 of FIG. 1.

In this position the weight of the patient exerted on the connecting arm 44 through the seat assembly maintains elastic member 100 in a fully compressed state inside its housing 94. The seat assembly rests on the ground through pads 54 and 56 (FIG. 1). Arm 44 is therefore in a lower and horizontal position and pad 102 is distant from the inner face 90d1 of upper face 90d. In this position connecting member 90 is further maintained against the indexed face 72a in the working indexed position thanks to the patient's weight. To be noted that, in the absence of a patient on the seat part, elastic member 80 is sufficiently sized to urge the connecting member 90 downwardly against the indexed face 72a in the working indexed position or in any other rest indexed position.

When the patient stands up (the examination underwent by the patient has come to an end), the weight of the patient does no longer compensate for the upward force exerted by elastic member 100. The latter then biases the connecting arm 44 upwardly. As the end 44a is pivotally mounted about pivot axis 94a, the upward movement of arm 44 causes a pivoting motion thereof about axis 94a and pad 102 abuts against inner face 90d1. The force exerted by elastic member 100 is not great enough to cause the connecting member 90 to raise.

Figure 7:
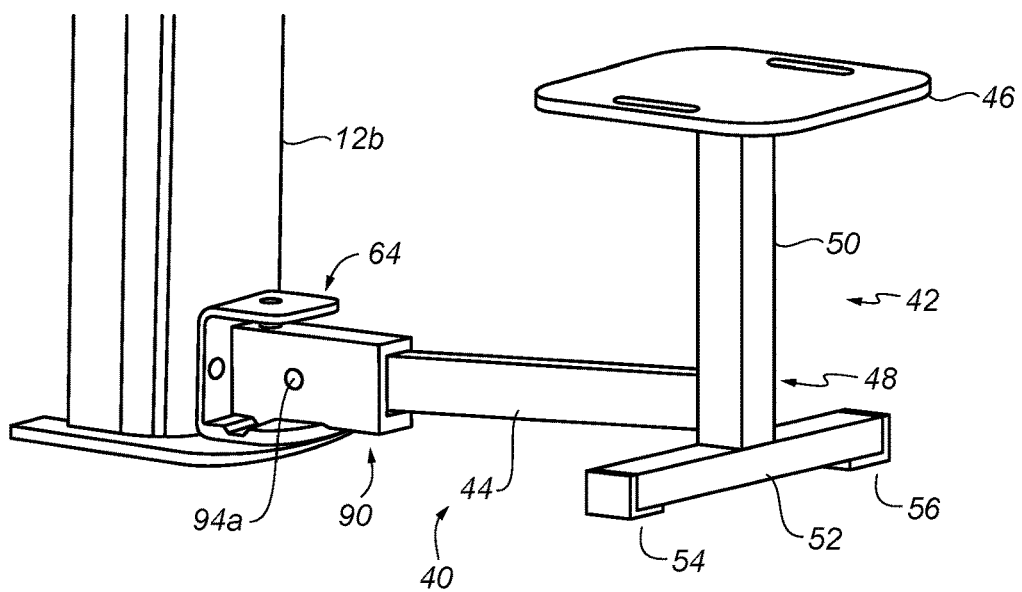
FIG. 7 illustrates a median working position of the seat arrangement of FIG. 1.

This upper position of connecting arm 44 corresponds to a rest position for the arm in the absence of any patient on the seat assembly. Such a position is illustrated in FIG. 7 where the seat arrangement 40 is still in an working indexed position. As represented, the arm 44 has pivoted upwardly about axis 94a which has caused an elevation of seat assembly 42 relative to the ground. The pads 54 and 56 are therefore no longer in contact with the ground. As shown on FIG. 7, the arm 44 and connecting member or casing 90 are no longer parallel to each other. This elevated position of seat assembly 42 makes it easy for a user of the apparatus to manually rotate the seat arrangement about vertical. If the pads were still on the ground the user would have to raise the seat arrangement first before rotating it. In the elevated position the user can simply drive the seat arrangement into a rotating motion towards one of the two rest indexed positions of FIGS. 2 and 3 so as to stow away the seat arrangement 40 in a location away from the working are of FIG. 1. The rotating motion is made easy thanks to the beveled edges of the indexed face 72a which help connecting member 90 to leave the groove in which it is positioned as explained above. FIGS. 2 and 3 illustrate the seat arrangement 40 in each of the two rest indexed positions with the position of the arm 44 in the above-described rest position for FIG. 7. In each of these rest positions the seat arrangement 40 abuts against bracket 64 which prevents any further rotating motion.

Other embodiments illustrated in FIGS. 8 to 13B show other possible pivoting seat arrangements that are integrated in an extra-oral dental imaging apparatus. The apparatus may be apparatus 10 of FIG. 1 or an apparatus similar to and that comprises at least: a support frame and a gantry that supports an x-ray source and at least one x-ray sensor in correspondence with the x-ray source, the gantry being movable relative to the support frame. The apparatus will not be described any further in the following embodiments.

Although the apparatus that integrates the seat arrangement is not always represented in the drawings of the following embodiments, it is to be understood as being implicitly part of the described embodiments. In the following embodiments each seat arrangement is connected to the support frame and is movable between at least two distinct positions: a working position and at least one rest position, e.g. two rest positions as described above with reference to FIGS. 1 to 7.

Figure 8:
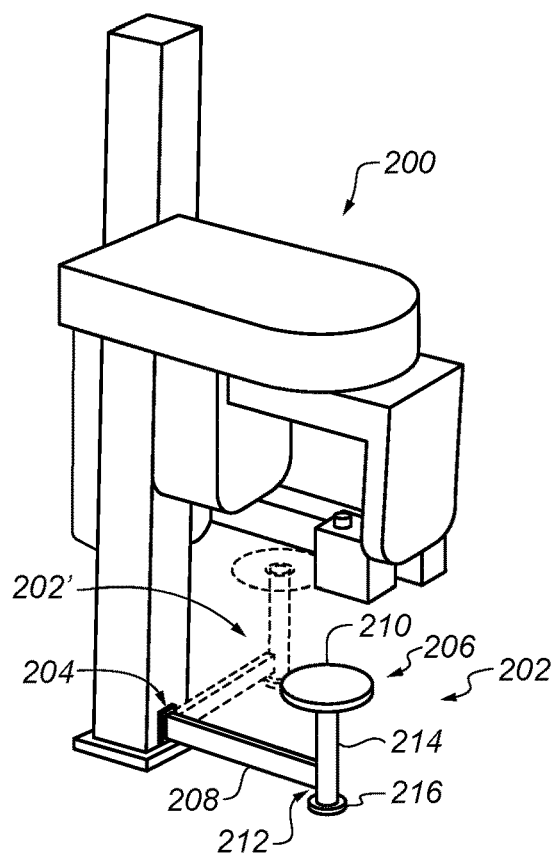
FIGS. 8 to 14 illustrate further possible embodiments of seat arrangements.

FIG. 8 represents an apparatus 200 which comprises a seat arrangement 202 that is pivotally mounted relative to the support frame. All that has been described above for the pivoting assembly can apply here and will not be repeated.

Seat arrangement 202 is pivotally mounted through a pivoting assembly 204 and comprises a seat assembly 206 as well as a connecting arm 208. Seat assembly 206 comprises a seat part 210 and a leg assembly 212 for ground support. Leg assembly 212 further comprises a vertical central member 214 and a baseplate 216, e.g. circular in shape. The seat arrangement 202 is also represented as 202' in a pivoted position after a 90° pivoting motion has been made from the working median position.

Figure 9:
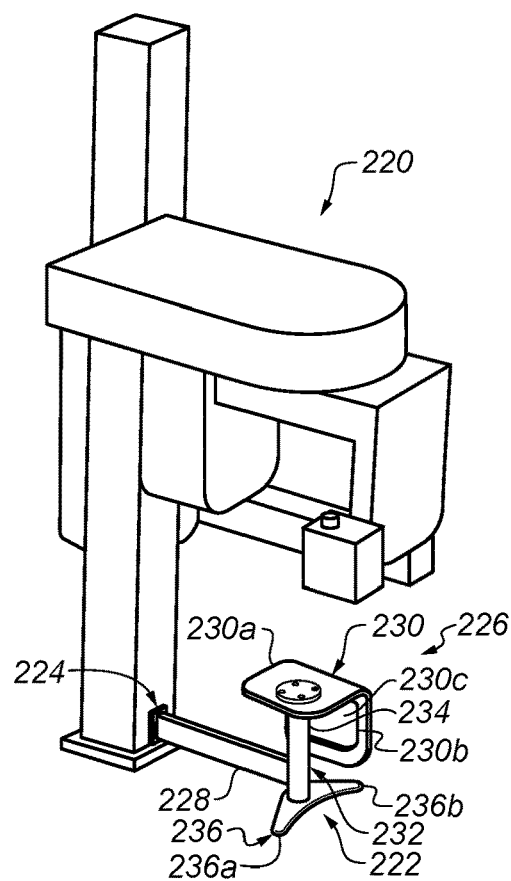

FIG. 9 represents an apparatus 220 having a seat arrangement 222 that is also pivotally mounted relative to the support frame through a pivoting assembly 224. Seat arrangement 222 comprises a seat assembly 226 as well as a connecting arm 228. Seat assembly 226 comprises a seat part 230 and a leg assembly 232 for ground support. Leg assembly 232 further comprises a vertical central member 234 and a baseplate 236. Baseplate 236 comprises two elongated portions 236a, 236b that are each coupled to vertical central member 234 at one of their two opposite ends. The two portions 236a, 236b extend outwardly away from each other so as to substantially form a V shape. Baseplate 236 thus configured offers a more stable ground support than baseplate 216 of FIG. 8. Seat part 230 is substantially square in shape and not circular as in FIG. 8. Seat part 230 also includes, in addition to an horizontal portion 230a forming the seat, a vertical downwardly extending portion 230b which serves as a support for the legs of the patient. Portion 230b has been recessed or partly removed in its middle part to make the seat part 230 lighter.

Figure 10:
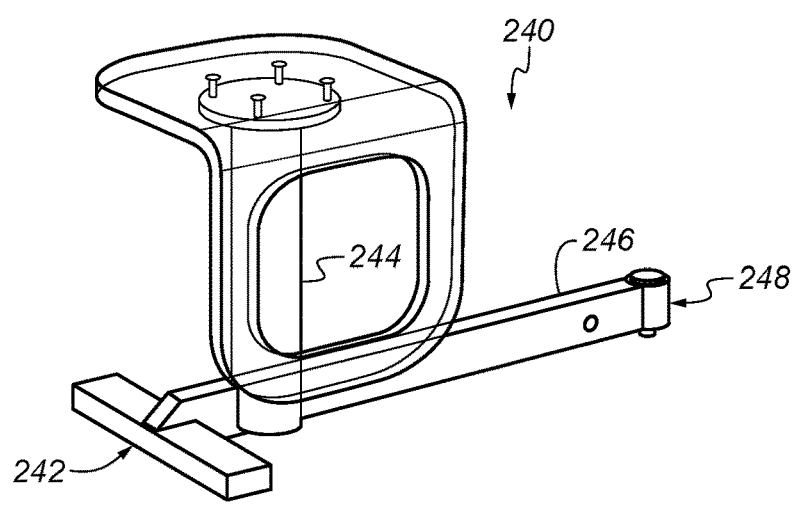

FIG. 10 illustrates a variant embodiment to FIG. 10 in which only the seat arrangement 240 has been illustrated. This arrangement mainly differs from seat arrangement 222 in that:
the baseplate 242 for ground support has a rectilinear shape substantially as transverse member 52 of FIG. 1;
vertical central member 244 is axially shifted along the arm 246 towards the pivoting assembly 248 so as to be away from baseplate 242.

Figure 11:
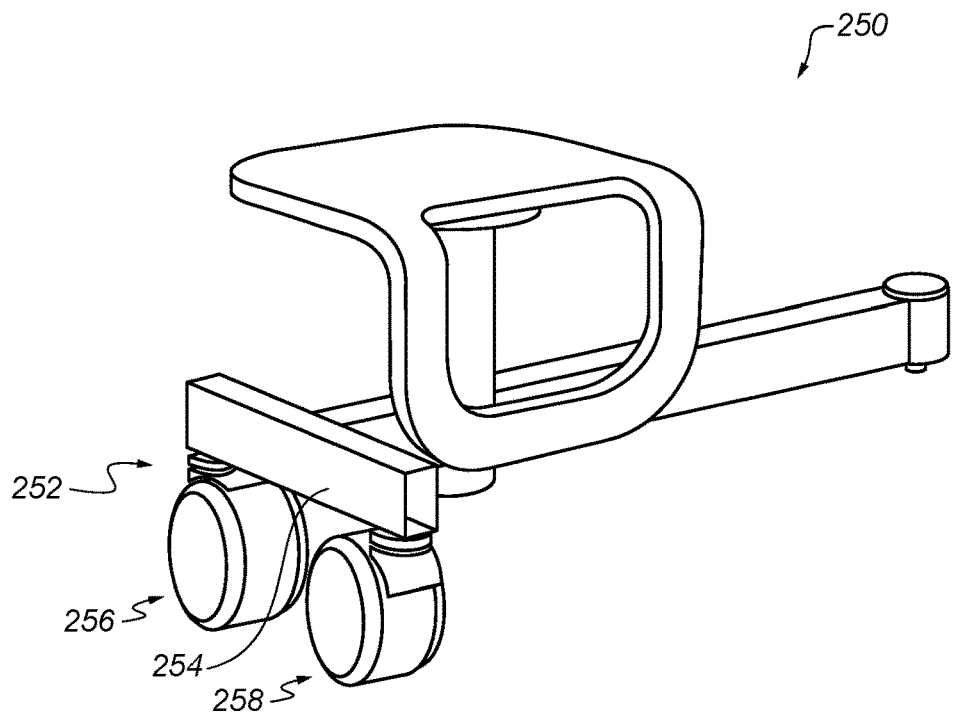

FIG. 11 illustrates a variant embodiment to FIG. 10 in which only the seat arrangement 250 has been illustrated. This arrangement mainly differs from seat arrangement 240 in that the baseplate 252 for ground support is a transverse member 254 mounted on casters 256, 258, e.g. in the number of two. The casters are disposed in alignment with member 254 which may take the form a rail oriented downwardly. The casters are mounted through mounting support members (not represented) located inside the rail. This arrangement provides further help for manually pivoting the seat arrangement.

Figure 12:
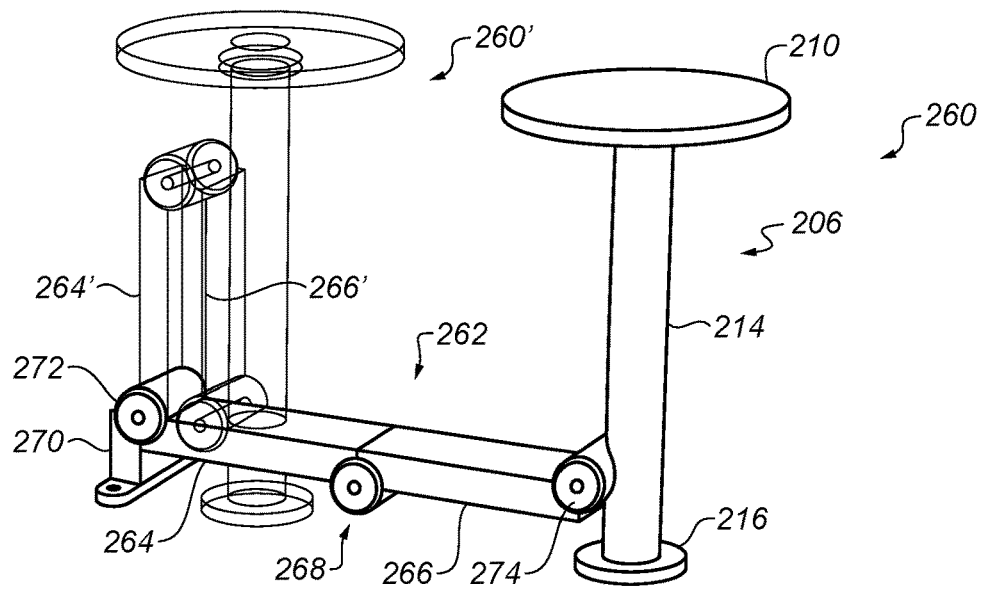

FIG. 12 illustrates a further embodiment in which only the seat arrangement 260 has been illustrated in a deployed or unfolded position and in a retracted or folded position referred to as 260'. The seat arrangement 260 takes over some of the components of seat arrangement 202 in FIG. 8:

the seat assembly 206 with its seat part 210, vertical member 214 and baseplate 216. However, the seat arrangement 260 comprises a connecting arm 262 that is an hinged arm. Hinged arm 262 includes two elongated portions 264, 266 that are linked together by a first hinge mechanism 268. Elongated portion 264 is connected to a support frame a member of which only 270 has been represented. This member may be attached to baseplate 62 of FIG. 1. Elongated portion 266 is connected to vertical member 214 of seat assembly 206.

The connections between the elongated portions 264, 266 and support frame 270 and seat assembly 206 respectively comprise second 272 and third 274 hinge mechanisms respectively.

Each of the above three hinge mechanisms may be the same and may include a pivoting assembly of the same type as that of FIG. 4. Contrary to the pivoting assembly of FIG. 4, the pivot axis of each hinge mechanism is horizontal.

In an extended or deployed position the two elongated portions 264, 266 are in alignment to place the seat arrangement in the working position.

To switch between the extended position and a retracted or folded position the seat assembly 206 is pushed back by the user so that the two elongated portions 264, 266 can pivot relative to the three hinge mechanisms.

In the retracted or folded position the two elongated portions referred to as 264', 266' are placed one against the other in a substantially parallel relationship. With this configuration the seat assembly has thus been placed in a stowed away or rest position which leaves freed the working area under the gantry of the apparatus (not represented). This arrangement is more compact than the previous ones.

Figure 13A:
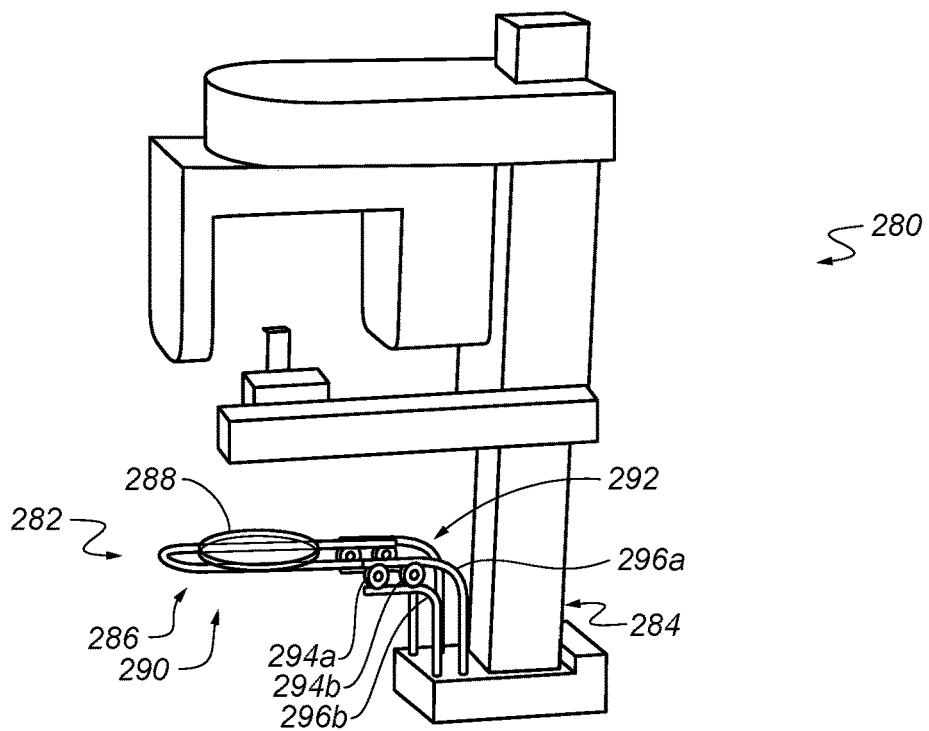
Figure 13B:
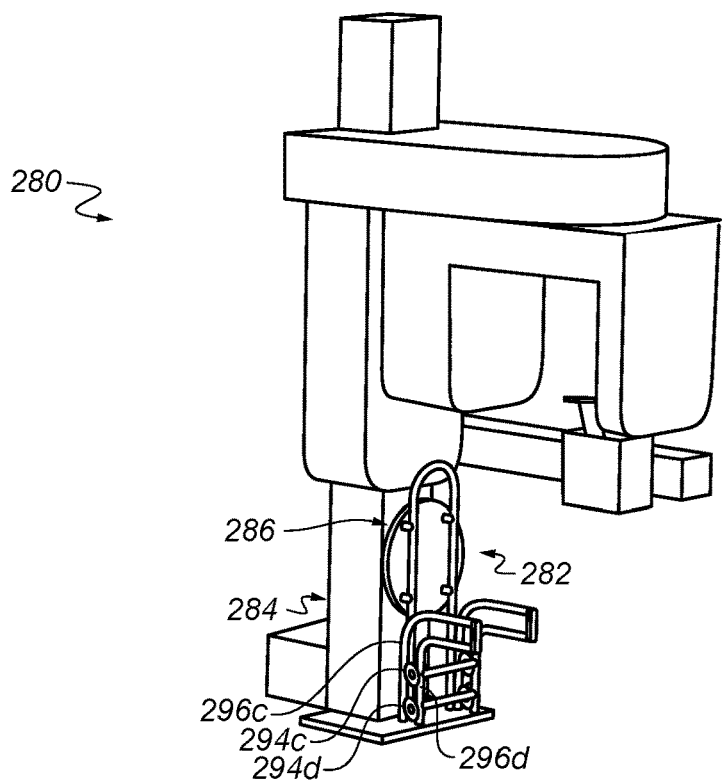

FIGS. 13A and 13B illustrate a further embodiment of an apparatus 280 comprising a seat arrangement 282 of another type which is configured to move in 3D e.g., both pivot and translate, relative to the support frame 284.

The seat arrangement comprises a seat assembly 286 with a seat part 288 coupled to a movable supporting structure 290 which is slidably mounted on a fixed rail structure 292. Movable supporting structure 290 includes side rollers which are located each between two elongated members defining a rail path therebetween closed at its two opposite ends and which serve as guide rails. Rail structure 292 is fixed to the support frame. More particularly, structure 290 includes two sets of two rollers 294a-d visible on FIGS. 13A-B and acts as a carriage. Each roller of each set is positioned inside a rail path defined by two elongated members 296a-b and 296c-d. The two pairs of elongated members 296a-b and 296c-d are transversally spaced apart from each other from a distance corresponding to the distance between the two rollers of each set. The two pairs of elongated members 296a-b and 296c-d are shaped so as to substantially take the form of a L in a lying position. The seat assembly 286 is therefore manually moved along the L-shaped path from the working position of FIG. 13A to the rest position of FIG. 13B where the seat assembly is in a vertical stowed away position. Such an arrangement is convenient to use and provides a compact design. The members of the supporting structure 290 and fixed rail structure 290 may take the form of hollow cylindrical and curved tubes.

Figure 14:
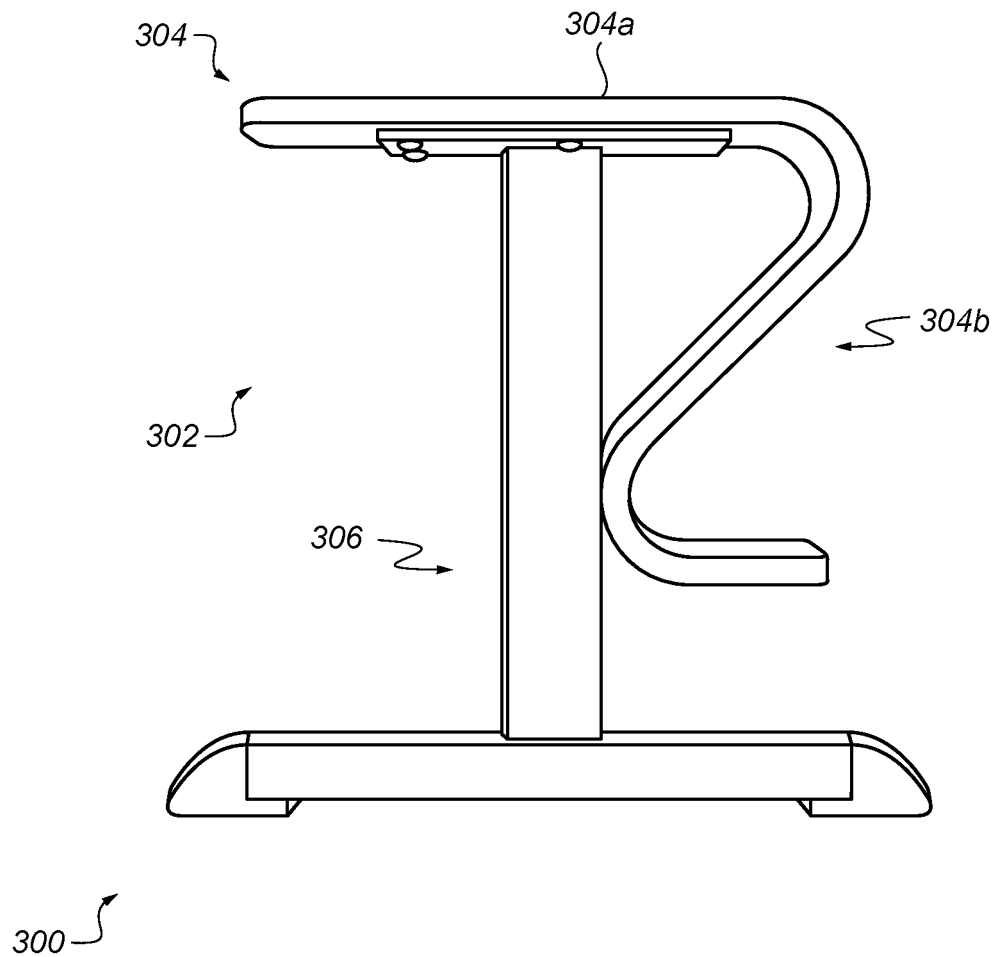

FIG. 14 illustrates a further embodiment in which only the seat arrangement 300 has been represented. This seat arrangement is similar to that of FIGS. 1 to 7 regarding the pivoting motion relative to the support frame of the apparatus.

The seat arrangement 300 comprises a seat assembly 302 with a seat part 304 and a leg assembly 306 for ground support. Seat assembly 302 differs from seat assembly 42 of FIGS. 1 to 7 in the configuration of its seat part. Seat part 304 includes a horizontal portion 304a on which the patient sits and a downwardly extending portion 304b in the form of an S or inverted S (when viewed from the opposite side) when viewed laterally as seen on FIG. 14. It could also be considered that the upper part of the S- or S-inverted shape extends horizontally to form horizontal portion 304a. The lower part of the S- or S-inverted shape serves as a footrest for the patient sitting on the seat part.

This configuration is asymmetrical as in FIGS. 10 and 11 since the patient can only sit according to one orientation. In contrast, the other configurations make it possible for the patient to be oriented according to several orientations, in particular two 180° opposite orientations.

Other possible seat arrangement embodiments may be envisaged within the scope of the invention.

Certain exemplary method and/or apparatus embodiments according to the application can provide exemplary seat arrangements that can reciprocally and repeatedly move between various different positions described above (e.g., at least one working position and at least one rest storage/rest position. Exemplary embodiments according to the application can include various features described herein (individually or in combination). Although embodiments of the present disclosure are illustrated using dental imaging apparatus, similar principles can be applied for other types of diagnostic imaging and for other anatomy.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by at least the following claims.

The invention claimed is:

1. An extra-oral dental imaging apparatus for obtaining a radiographic image of a patient, the apparatus comprising:
   a support frame,
   a gantry that supports an x-ray source and at least one x-ray sensor in correspondence with the x-ray source, the gantry being movable relative to the support frame,
   wherein the apparatus further comprises a seat arrangement that is movably connected to a support column of the support frame, enabling a rotational movement of the seat arrangement around the support column, and that is movable between at least two distinct positions:
   a working position in which the seat arrangement is located in a working area under the gantry, at least one rest position in which the seat arrangement is located away from the working area so as to leave clear the working area under the gantry for standing of the patient within the imaging area.

2. The dental imaging apparatus of claim 1, wherein the seat arrangement comprises a seat assembly and a connecting arm.

3. The dental imaging apparatus of claim 1, wherein the seat assembly comprises a seat part and a leg assembly restable in the working position on the ground within the working area for ground support of the patient, and positionable in the at least one rest position entirely outside of the working area.

4. The dental imaging apparatus of claim 1, wherein the seat arrangement is configured to pivot relative to the support frame.

5. The dental imaging apparatus of claim 4, wherein the seat arrangement is configured to pivot relative to the support frame through a pivoting assembly.

6. The dental imaging apparatus of claim 5, wherein the pivoting assembly comprises an indexed face which includes at least two indexed positions corresponding to said at least two distinct positions of the seat arrangement respectively, the seat arrangement being configured to pivot relative to the indexed face to move from one indexed position to another.

7. The dental imaging apparatus of claim 6, wherein the indexed face includes three indexed positions corresponding to three distinct positions of the seat arrangement respectively, namely the working position and two rest positions.

8. The dental imaging apparatus of claim 6, wherein the seat arrangement is urged against the indexed face through at least one elastic member.

9. The dental imaging apparatus of claim 6, wherein the seat arrangement comprises a connecting member that connects the connecting arm to the support frame, the connecting member being configured to pivot at one end relative to the indexed face of the pivoting assembly to move from one indexed position to another.

10. The dental imaging apparatus of claim 9, wherein the connecting member is connected at its opposite end to a first end of the connecting arm, the second opposite end of the connecting arm being connected to the seat assembly.

11. The dental imaging apparatus of claim 10, wherein the first end of the connecting arm is movably mounted relative to the connecting member in a vertical plane that includes the pivot axis of the pivoting assembly.

12. The dental imaging apparatus of claim 11, wherein the first end of the connecting arm is urged upwardly through at least one elastic member so that the connecting arm is urged in an upper rest position in the absence of any patient on the seat assembly.

13. The dental imaging apparatus of claim 11, wherein the first end of the connecting arm is pivotally mounted relative to the connecting member about a pivot axis that is perpendicular to the vertical plane.

14. The dental imaging apparatus of claim 1, wherein the seat arrangement is configured to both pivot and translate relative to the support frame.

15. An extra-oral dental imaging apparatus for obtaining a radiographic image of a patient, the apparatus comprising:
a support frame,
a gantry that supports an x-ray source and at least one x-ray sensor in correspondence with the x-ray source, the gantry being movable relative to the support frame,
wherein the apparatus further comprises a seat arrangement that is connected to the support frame and that is movable between at least two distinct positions:
a working position in which the seat arrangement is located in a working area under the gantry, and
at least one rest position in which the seat arrangement is located away from the working area so as to leave clear the working area under the gantry for standing of the patient within the imaging area,
wherein the seat arrangement comprises a seat assembly and a connecting arm, and the connecting arm is a hinged arm that includes two elongated portions that are linked together by a hinge mechanism.

16. A method for using an extra-oral dental imaging apparatus for obtaining a radiographic image of a patient, the apparatus comprising:
a support frame,
a gantry that supports an x-ray source and at least one x-ray sensor in correspondence with the x-ray source, the gantry being movable relative to the support frame,
a seat arrangement that is movably connected to a support column of the support frame, enabling a rotational movement of the seat arrangement around the support column,
wherein the method comprises moving the seat arrangement between at least two distinct positions:
a working position in which the seat arrangement is located in a working area under the gantry,
a rest position in which the seat arrangement is located away from the working area so as to leave clear the working area under the gantry for standing of the patient within the imaging area,
the method comprising:
moving the seat arrangement into the rest position; and
standing the patient within the imaging area.

17. The dental imaging apparatus of claim 1, wherein the rest position of the seat arrangement is outside a footprint of the gantry, where the footprint of the gantry is an area vertically beneath the gantry during the movement of the gantry relative to the support frame during an imaging process of the extra-oral dental imaging apparatus.

18. The dental imaging apparatus of claim 1, wherein the at least one rest position of the seat arrangement is outside a footprint of the gantry, where the footprint of the gantry is an area vertically beneath the gantry during an imaging process of the extra-oral dental imaging apparatus using the gantry.

19. The dental imaging apparatus of claim 1, wherein the seat arrangement comprises a seat assembly, a connecting arm, and a connecting member that connects the connecting arm to the support frame, the connecting member being configured to pivot using an indexed face to move from the working position and the at least one rest position.

20. An extra-oral dental imaging apparatus for obtaining a radiographic image of a patient, the apparatus comprising:
a support frame,
a gantry that supports an x-ray source and at least one x-ray sensor in correspondence with the x-ray source, the gantry being movable relative to the support frame,
wherein the apparatus further comprises a seat arrangement that is moveably connected to the support frame, enabling a rotational movement of the seat arrangement around the support frame, and that is movable between at least two distinct positions:
a working position in which the seat arrangement is located in a working area under the gantry, at least one rest position in which the seat arrangement is located away from the working area so as to leave clear the working area under the gantry.

\* \* \* \* \*